US008633945B2

(12) United States Patent
Nakamura et al.

(10) Patent No.: US 8,633,945 B2
(45) Date of Patent: Jan. 21, 2014

(54) X-RAY DIAGNOSTIC APPARATUS AND IMAGE PROCESSING APPARATUS

(75) Inventors: Keisuke Nakamura, Utsunomiya (JP); Shingo Abe, Nasushiobara (JP); Yoshinori Shimizu, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 13/479,384

(22) Filed: May 24, 2012

(65) Prior Publication Data
US 2012/0229504 A1 Sep. 13, 2012

Related U.S. Application Data

(63) Continuation of application No. PCT/JP2012/051129, filed on Jan. 19, 2012.

(30) Foreign Application Priority Data

Jan. 19, 2011 (JP) ................................. 2011-008675

(51) Int. Cl.
*G09G 5/00* (2006.01)
*A61B 6/00* (2006.01)
*A61M 5/00* (2006.01)

(52) U.S. Cl.
USPC ............................ 345/629; 600/431; 600/432

(58) Field of Classification Search
USPC .................................. 345/629; 600/432, 431
See application file for complete search history.

(56) References Cited

U.S. PATENT DOCUMENTS 7,283,614 B2 * 10/2007 Nakano et al. ............. 378/98.12
2011/0313287 A1 * 12/2011 Komatsu et al. ............. 600/432

FOREIGN PATENT DOCUMENTS

| JP | 2007-21006 | | 2/2007 |
| JP | 2009-225 | | 1/2009 |
| JP | 2011-55967 | | 3/2011 |
| JP | 2011055967 A | * | 3/2011 |
| WO | WO 2010/101184 A1 | | 9/2010 |

OTHER PUBLICATIONS

Translation from JP, 2011-055967, Urushiya Hiroyuki, "Image Processing Device, Image Processing Method, and Program", Mar. 24, 2011.*
International Search Report and Written Opinion of the International Searching Authority issued Feb. 21, 2012, in PCT/JP2012/051129 (with English-language translation of the International Search Report).

* cited by examiner

*Primary Examiner* — Kee M Tung
*Assistant Examiner* — Haixia Du
(74) *Attorney, Agent, or Firm* — Oblon, Spivak, McClelland, Maier & Neustadt, L.L.P.

(57) ABSTRACT

According to one embodiment, an image processing apparatus includes following units. The correspondence table describes a relationship between blood vessel contrasts and reference contrast medium concentrations and reference X-ray conditions. The acquisition unit acquires a blood vessel contrast by referring to the correspondence table based on the planned value of a contrast medium concentration and the X-ray condition. The calculation unit calculates a predictive pixel value of a region of interest set on the X-ray image based on the blood vessel contrast. The display unit displays the X-ray image while superimposing a partial image with the predictive pixel value on the region of interest.

9 Claims, 8 Drawing Sheets

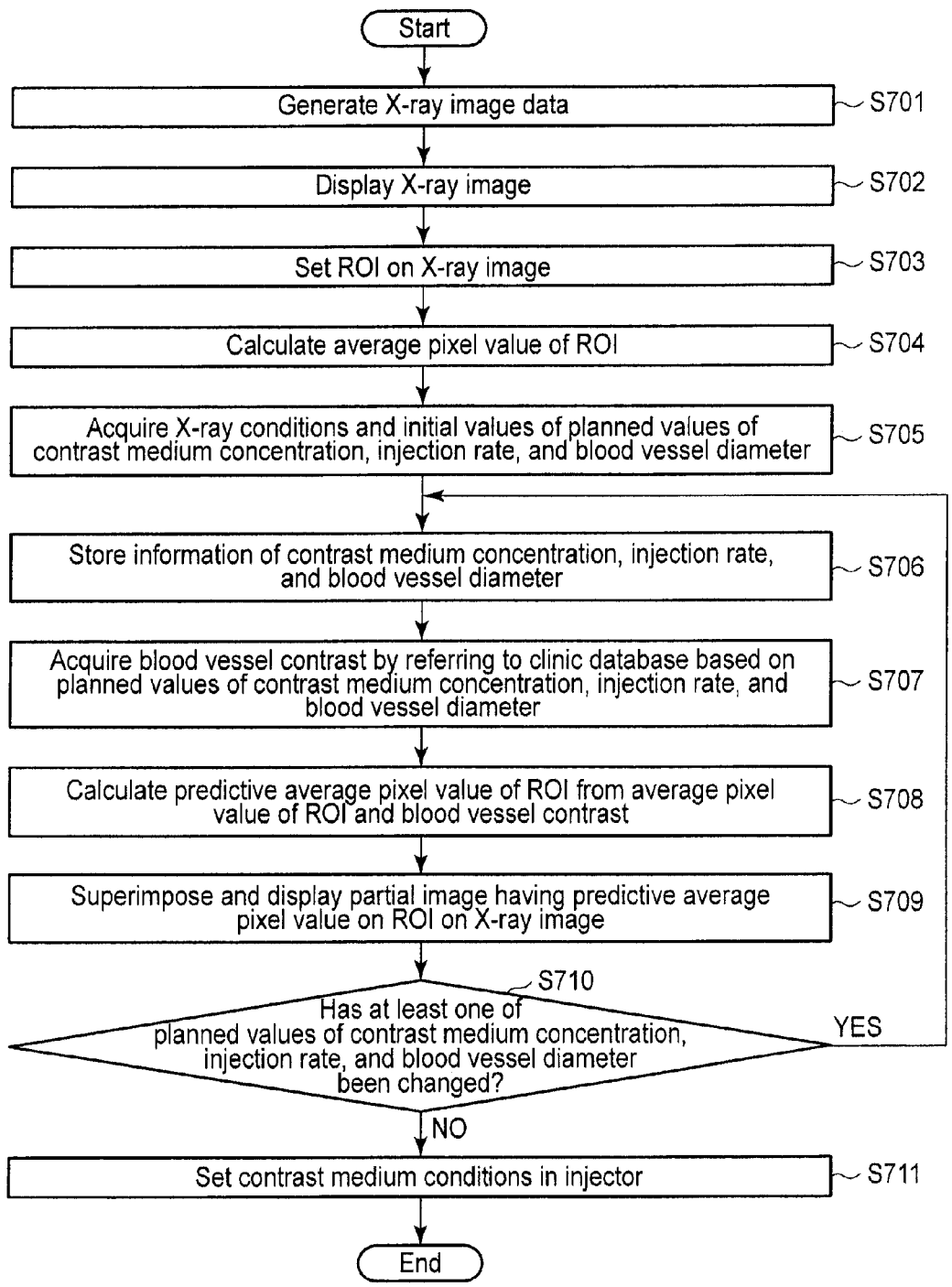
F I G. 7

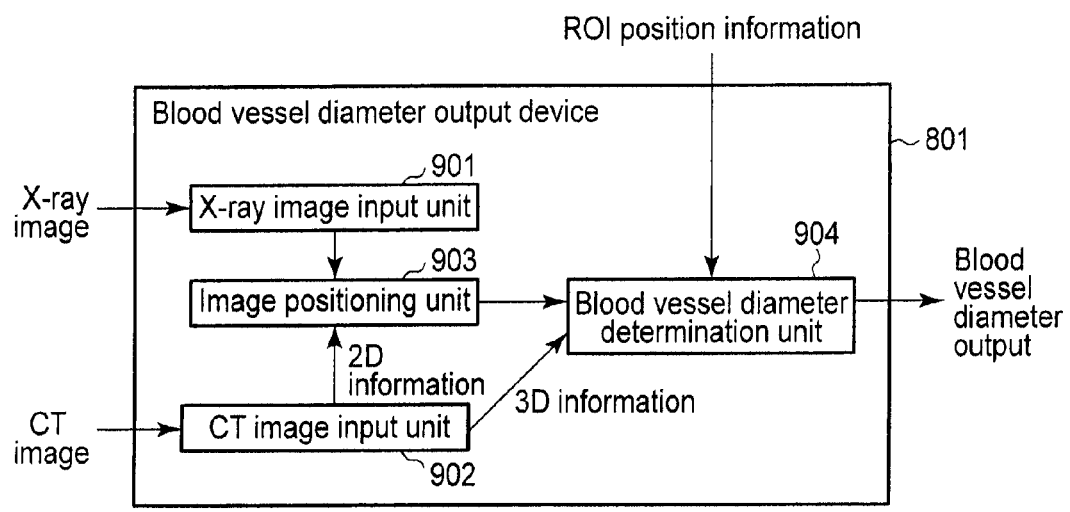
F I G. 9

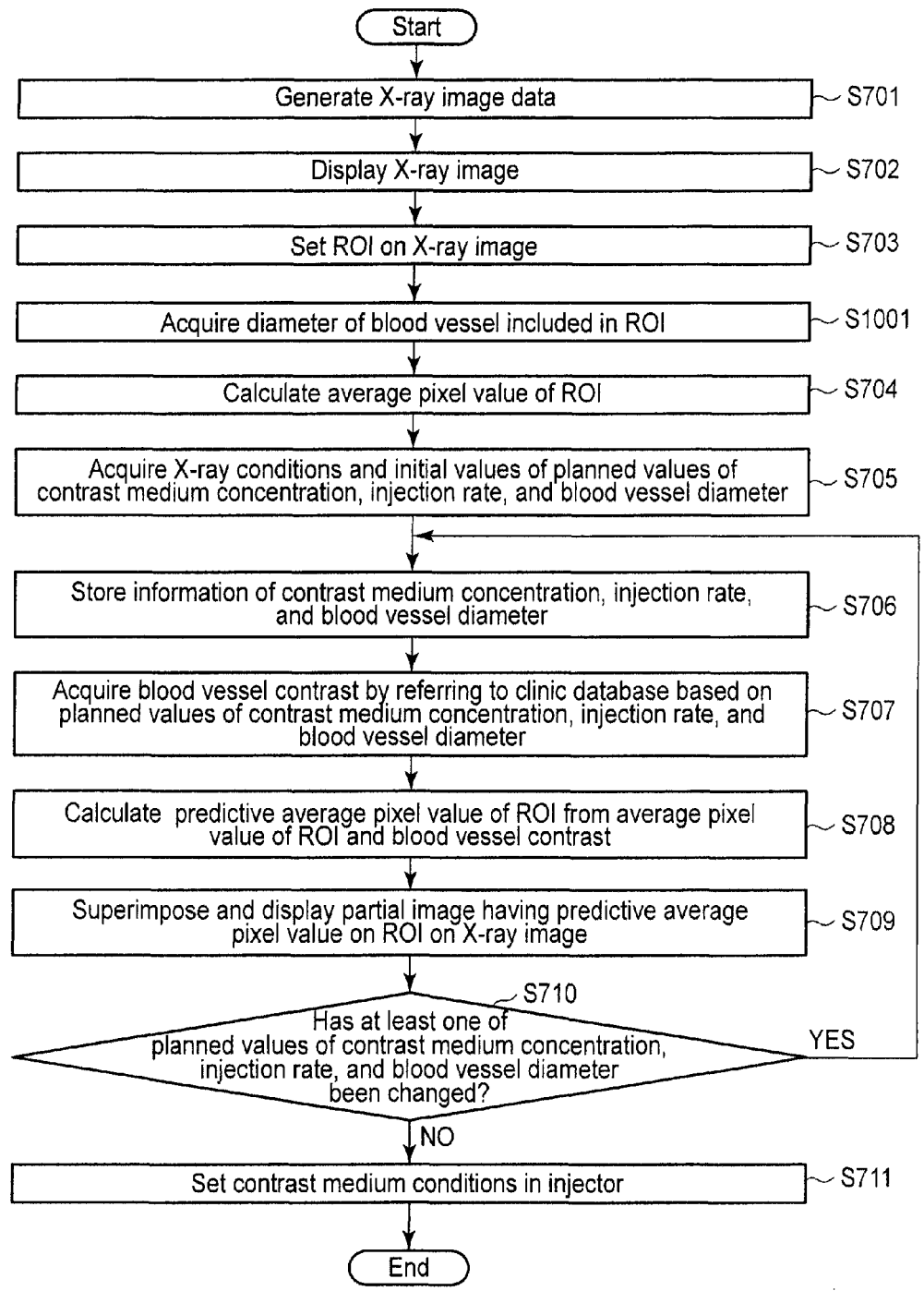
F I G. 10

US 8,633,945 B2

X-RAY DIAGNOSTIC APPARATUS AND IMAGE PROCESSING APPARATUS

CROSS REFERENCE TO RELATED APPLICATIONS

This application is a Continuation Application of PCT Application No. PCT/JP2012/051129, filed Jan. 19, 2012 and based upon and claiming the benefit of priority from prior Japanese Patent Application No. 2011-008675, filed Jan. 19, 2011, the entire contents of all of which are incorporated herein by reference.

FIELD

Embodiments described herein relate generally to an X-ray diagnostic apparatus and an image processing apparatus.

BACKGROUND

An angiographic examination or intravascular treatment using an X-ray diagnostic apparatus uses a contrast medium to grasp the shape and position of a blood vessel. In general, the concentration of a contrast medium to be injected into an object is fixed within one procedure. The blood vessel contrast on an angiographic image captured while a contrast medium is injected in an object varies depending on imaging conditions (e.g., an object, X-ray conditions, and an imaging angle). The contrast medium in use does not always have a proper concentration. For this reason, depending on the object, a contrast medium having an excessively high concentration is used sometimes. In another case, a desired blood vessel contrast cannot be obtained on an angiographic image due to the low concentration of contrast medium, and X-ray imaging is performed again upon changing contrast medium conditions such as a contrast medium concentration and an injection rate.

Unnecessarily injecting a contrast medium into an object in this manner may increase the possibility of occurrence of nephropathy in the object. Therefore, in order to reduce the amount of contrast medium used, an X-ray diagnostic apparatus is required to be capable of predicting and displaying a blood vessel contrast in an angiographic image before capturing of the angiographic image.

BRIEF DESCRIPTION OF THE DRAWINGS

FIG. 7 is a flowchart schematically showing an example of image processing in the X-ray diagnostic apparatus in FIG. 1;

FIG. 9 is a block diagram schematically showing the blood vessel diameter output device shown in FIG. 8; and FIG. 10 is a flowchart schematically showing an example of image processing in the X-ray diagnostic apparatus shown in FIG. 8.

DETAILED DESCRIPTION

In general, according to one embodiment, an image processing apparatus includes a display unit, a data storage unit, an input unit, an acquisition unit, a calculation unit, and a control unit. The display unit is configured to display an X-ray image. The data storage unit is configured to store a first correspondence table describing a relationship between blood vessel contrasts and reference contrast medium concentrations and reference X-ray conditions. The input unit is configured to receive input information including a planned value of a concentration of a contrast medium planned to be injected and an X-ray condition planned to be applied when an angiographic image is captured. The acquisition unit is configured to acquire a blood vessel contrast by referring to the reference contrast medium concentrations and the reference X-ray conditions in the first correspondence table based on the planned value and the X-ray condition. The calculation unit is configured to calculate a predictive pixel value of a region of interest set on the X-ray image based on the acquired blood vessel contrast and a pixel value of the region of interest. The control unit is configured to control the display unit to display the X-ray image while superimposing a partial image having the calculated predictive pixel value on the region of interest.

The image processing apparatus according the embodiment can predict and display a blood vessel contrast on an angiographic image before capturing of the angiographic image. According to another embodiment, there is provided an X-ray diagnostic apparatus including the image processing apparatus.

An X-ray diagnostic apparatus and an image processing apparatus according to an embodiment will be described hereinafter with reference to the accompanying drawings. The following embodiment will exemplify a case in which an X-ray diagnostic apparatus includes an image processing apparatus. However, an image processing apparatus according to the embodiment can be applied to not only an X-ray diagnostic apparatus but also an X-ray computed tomography apparatus which obtains a tomogram of an object by X-ray irradiation. In the embodiments, like reference numbers denote like elements, and duplication of explanation will be avoided.

First Embodiment

Figure 1:
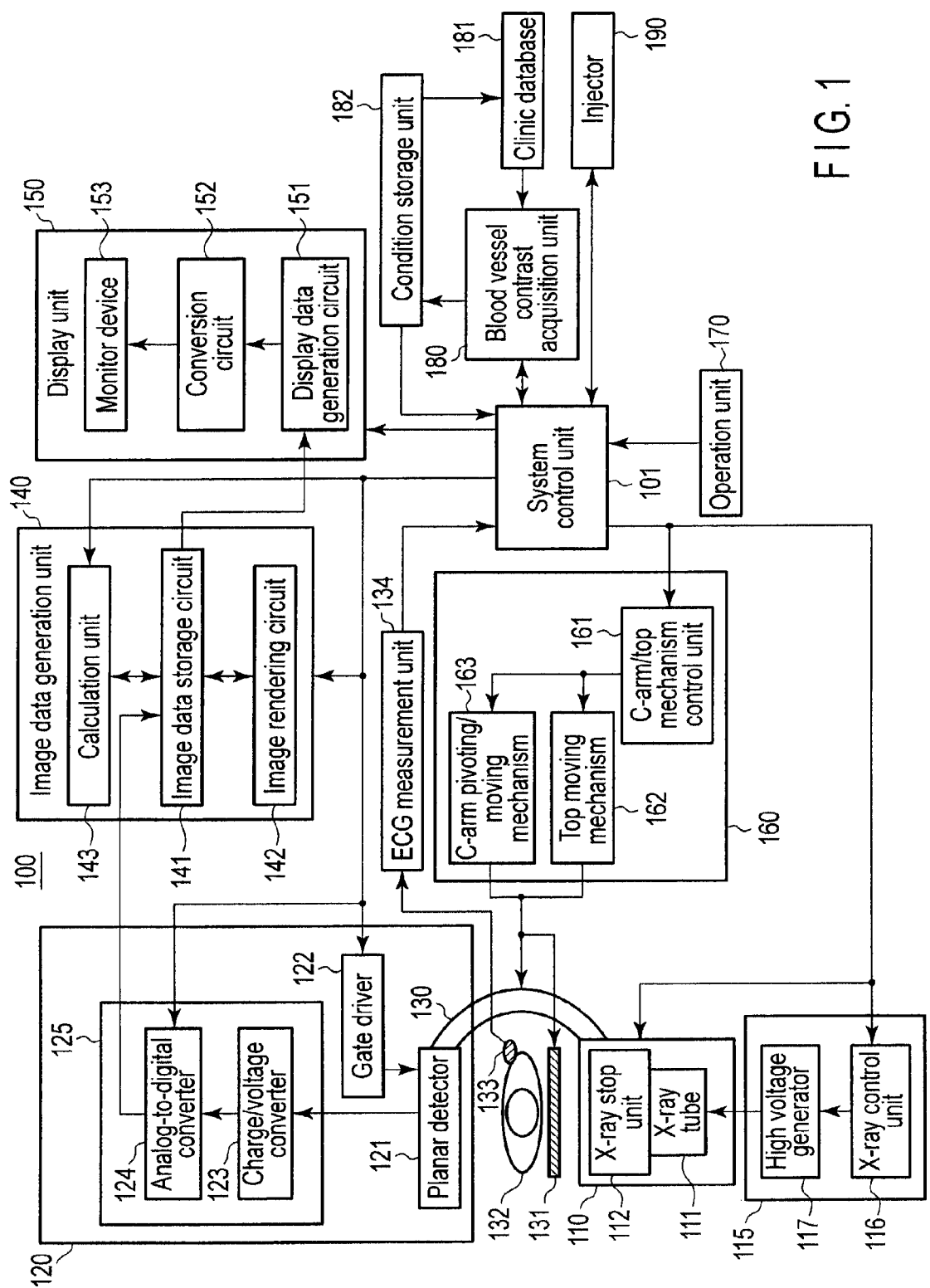
FIG. 1 is a block diagram schematically showing an X-ray diagnostic apparatus according to the first embodiment.
Figure 2:
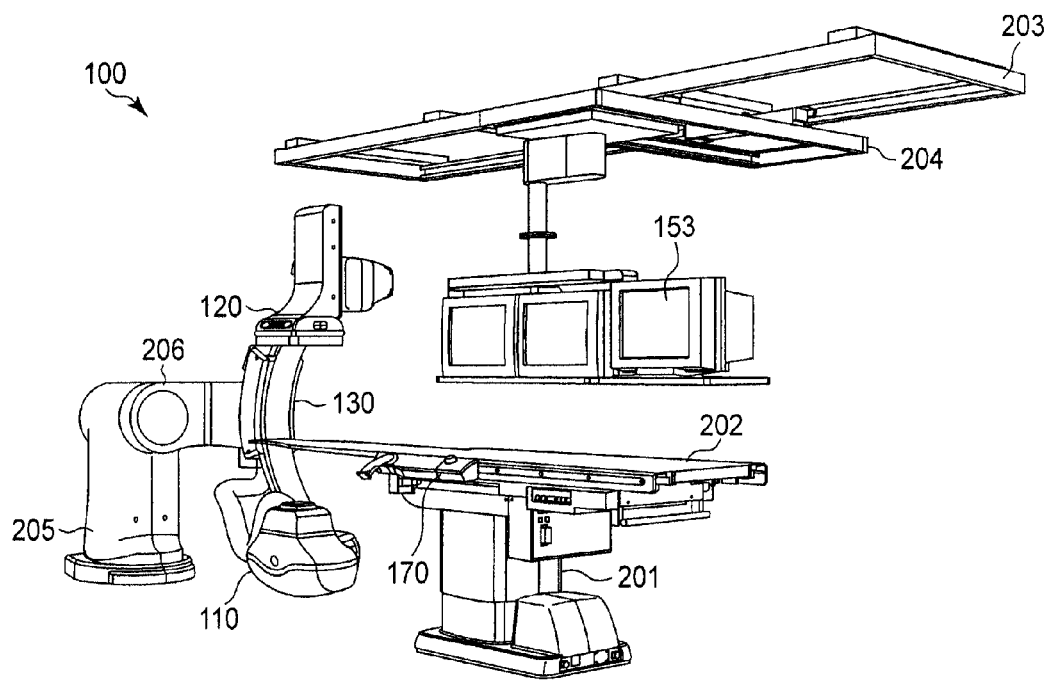
FIG. 2 is a perspective view showing an example of the outer appearance of the X-ray diagnostic apparatus in FIG. 1.

FIG. 1 is a block diagram schematically showing an X-ray diagnostic apparatus 100 according to an first embodiment. FIG. 2 is a perspective view schematically showing the outer appearance of the X-ray diagnostic apparatus 100. As shown in FIG. 2, the X-ray diagnostic apparatus 100 shown in FIG. 1 includes a C-arm 130 having an almost C shape. The C-arm 130 is pivotally and movably supported by an arm support portion 206. The arm support portion 206 is provided on a column 205.

The C-arm 130 has one end provided with an X-ray generation unit 110 which generates X-rays, and the other end provided with an X-ray detection unit 120 which detects the X-rays emitted from the X-ray generation unit 110 and transmitted through an object (shown in FIG. 1) 132. The X-ray generation unit 110 and the X-ray detection unit 120 are arranged so as to face each other through the object 132 placed on a bed 202. A top 131 shown in FIG. 1 is movably provided on the bed 202. The object 132 is placed on the top 131. The bed 202 is supported by a column 201 shown in FIG. 2. An operation unit 170 is provided on the bed 202.

The ceiling is provided with a support portion 203 including two slide rails. The support portion 203 supports a monitor holding portion 204 so as to allow it move along the slide rails. A plurality of monitor devices 153 are held on the monitor holding portion 204. As the monitor devices 153, a cathode-ray tube (CRT) display, a liquid crystal display (LCD), and the like can be used.

As shown in FIG. 1, a mechanism unit 160 drives the C-arm 130 and the top 131. The mechanism unit 160 includes a C-arm/top mechanism control unit 161, a top moving mechanism 162, and a C-arm pivoting/moving mechanism 163. The C-arm/top mechanism control unit 161 generates driving signals for driving the C-arm 130 and the top 131 in accordance with moving control instructions from a system control unit 101. The top moving mechanism 162 moves the top 131 by being operated by a driving signal from the C-arm/top mechanism control unit 161. The C-arm pivoting/moving mechanism 163 moves the C-arm 130 and also makes the C-arm 130 pivot about the body axis of the object 132 by being operated by driving signals from the C-arm/top mechanism control unit 161.

An electrocardiogram (ECG) monitor terminal 133 is attached to the object 132 placed on the top 131. The ECG monitor terminal 133 sends a signal to an ECG measurement unit 134. The ECG measurement unit 134 generates electrocardiogram data of the object 132 based on a signal from the ECG monitor terminal 133 and sends the data to the system control unit 101.

The X-ray diagnostic apparatus 100 further includes an injector 190 which injects a contrast medium into the object 132. For example, the injector 190 includes an injection head for injecting a contrast medium into a blood vessel of the object 132 and an injection control unit which controls the operation of the injection head. In addition, the injection head includes a cylinder filled with a contrast medium. Contrast medium conditions are set for the injector 190. The conditions include the concentration of contrast medium charged in the cylinder and the rate (injection rate) at which the contrast medium is injected into the object. The injector 190 executes injection of a contrast medium in accordance with an injection control command from the system control unit 101. Note that the user may directly operate the injector 190 to inject a contrast medium. The injector 190 may take the form that can adjust the concentration of contrast medium in accordance with contrast medium conditions.

A high-voltage generation unit 115 is connected to the X-ray generation unit 110. The high-voltage generation unit 115 applies a high voltage to the X-ray generation unit 110. More specifically, the X-ray generation unit 110 includes an X-ray control unit 116 and a high-voltage generator 117. The X-ray control unit 116 receives an X-ray condition command from the system control unit 101, generates a voltage application control signal for the generation of the voltage designated by this X-ray condition command, and sends the signal to the high-voltage generator 117. For example, X-ray conditions include a tube voltage to be applied between the electrodes of an X-ray tube 111 in the X-ray generation unit 110, an X-ray irradiation time, and an X-ray irradiation timing. The high-voltage generator 117 generates a high voltage in accordance with a voltage application control signal received from the X-ray control unit 116 and applies the voltage to the X-ray generation unit 110.

The X-ray generation unit 110 includes the X-ray tube 111 and an X-ray stop unit 112. The high-voltage generator 117 applies a high voltage to the X-ray tube 111 so that the X-ray tube 111 generates X-rays. The X-ray stop unit 112 is arranged between the X-ray tube 111 and the object 132 to limit the irradiation field of X-rays emitted from the X-ray tube 111 to the object 132.

The X-ray detection unit 120 detects the X-rays emitted from the X-ray generation unit 110 and transmitted through the object 132. More specifically, the X-ray detection unit 120 includes a planar detector 121, a gate driver 122, and a projection data generation unit 125. The planar detector 121 includes a plurality of two-dimensionally arrayed semiconductor detection elements. The gate driver 122 generates driving pulses for reading charges stored in the planar detector 121. The semiconductor detection elements of the planar detector 121 convert the X-rays transmitted through the object 132 into charges and store them. The stored charges are sequentially read by the driving pulses supplied from the gate driver 122.

The projection data generation unit 125 converts the charges read from the planar detector 121 into projection data corresponding to the amount of X-rays detected. More specifically, the projection data generation unit 125 includes a charge/voltage converter 123 and an analog-to-digital converter 124. The charge/voltage converter 123 converts each charge read from the planar detector 121 into a voltage signal. The analog-to-digital converter 124 converts the voltage signal output from the charge/voltage converter 123 into a digital signal and outputs it as projection data.

An image data generation unit 140 sequentially receives projection data from the projection data generation unit 125, and generates X-ray image data of the object 132 based on the received projection data. The X-ray image data is simply referred to as the image data hereinafter. More specifically, the image data generation unit 140 includes an image data storage circuit 141 and an image rendering circuit 142. The image data storage circuit 141 sequentially stores the projection data generated by the projection data generation unit 125. The image rendering circuit 142 generates image data by performing image processing such as filtering for the projection data stored in the image data storage circuit 141. The image data storage circuit 141 stores the generated image data. The image rendering circuit 142 performs image processing such as combining processing for image data, as needed.

The image data generation unit 140 further includes a calculation unit 143. The calculation unit 143 calculates the average pixel value of a region of interest (ROI) set on an X-ray image. In the embodiment, the user sets an ROI on the X-ray image displayed on the monitor devices 153 by operating the operation unit 170. The average pixel value of an ROI indicates the average value of the pixel values of a plurality of pixels included in the ROI. The calculation unit 143 also calculates a predictive average pixel value (referred to as the predictive pixel value) of the ROI based on the calculated average pixel value of the ROI and a blood vessel contrast (to be described later). As will be described later, the X-ray diagnostic apparatus 100 according to the embodiment can predict a blood vessel contrast on an angiographic image before capturing of the angiographic image, and display the prediction result as an ROI density on an X-ray image captured before injection of a contrast medium. The predictive average pixel value of the ROI calculated by the calculation unit 143 is used as the pixel value of each pixel in the ROI when predicting and displaying a blood vessel contrast.

Figure 3:
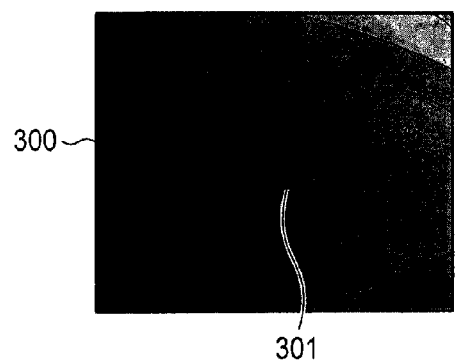
FIG. 3 is a view showing an example of the X-ray image displayed on a monitor device shown in FIG. 1.

A display unit 150 is connected to the image data storage circuit 141. The display unit 150 displays the image data generated by the image data generation unit 140 as an X-ray image. More specifically, the display unit 150 includes a display data generation circuit 151, a conversion circuit 152, and the plurality of monitor devices 153. The display data generation circuit 151 receives image data stored in the image data storage circuit 141 and generates display data to be displayed on each monitor device 153. The conversion circuit 152 converts the display data generated by the display data generation circuit 151 into a video signal and passes it to each monitor device 153. Each monitor device 153 displays an X-ray image 300 of the object 132, as shown in FIG. 3.

The system control unit 101 controls each unit in the X-ray diagnostic apparatus 100. The operation unit (to be also referred to as an input unit) 170 is connected to the system control unit 101. The operation unit 170 includes, for example, various kinds of input devices such as a keyboard and a mouse, and passes operation signals to the system control unit 101 in accordance with the operations of the input devices. For example, as shown in FIG. 3, the user uses the operation unit 170 to set an ROI 301 on the X-ray image 300 displayed on the monitor devices 153. The shape of the ROI 301 is not limited to the square shown in FIG. 3, and may be an arbitrary shape such as a rectangle or circle.

The operation unit 170 also receives inputs from the user, e.g., planned values of contrast medium concentration, injection rate, and blood vessel diameter, and X-ray conditions. These planned values are used to predict a blood vessel contrast on an angiographic image. The user inputs, as a planned value of contrast medium concentration, the concentration of a contrast medium planned to be injected when capturing an angiographic image. The user inputs, as a planned value of injection rate, the rate at which the contrast medium is to be injected into the object 132 at the time of capturing an angiographic image. Moreover, the user inputs, as a planned value of blood vessel diameter, the blood vessel diameter of an examination or treatment target included in the ROI. The X-ray conditions input from the operation unit 170 are sent to the X-ray control unit 116 via the system control unit 101 and set.

A blood vessel contrast acquisition unit 180 is connected to the system control unit 101. The blood vessel contrast acquisition unit 180 receives input information, which includes the planned values of contrast medium concentration, injection rate, and blood vessel diameter and the X-ray conditions which are input from the operation unit 170. A condition storage unit 182 stores the planned values of contrast medium concentration, injection rate, and blood vessel diameter and the X-ray conditions.

The blood vessel contrast acquisition unit 180 acquires a blood vessel contrast by referring to a clinic database 181 based on the planned values of contrast medium concentration, injection rate, and blood vessel diameter and the X-ray conditions stored in the condition storage unit 182. The clinic database 181 holds a correspondence table describing the relationship between "blood vessel contrasts" and "contrast medium concentrations, injection rates, blood vessel diameters, and X-ray conditions", i.e., a correspondence table in which blood vessel contrasts are associated with contrast medium concentrations, injection rates, blood vessel diameters, and X-ray conditions. A blood vessel contrast is defined by, for example, the following expression:

$$C = \frac{P0 - P1}{P0} \quad \text{Equation (1)}$$

where C is a blood vessel contrast, P0 is the average pixel value of an ROI on an X-ray image before injection of a contrast medium, and P1 is the average pixel value of the ROI on an X-ray image after injection of the contrast medium. That is, a blood vessel contrast is obtained by acquiring X-ray image data before and after injection of a contrast medium in a state in which imaging conditions such as X-ray conditions and an imaging angle are fixed, setting an ROI at the same position on X-ray images before and after injection of the contrast medium, and dividing the difference between the average pixel value of the ROI on the X-ray image before injection of the contrast medium and the average pixel value of the X-ray image after injection of the contrast medium by the average pixel value of the ROI on the X-ray image before injection of the contrast medium. A correspondence table in the clinic database 181 is generated by performing X-ray imaging upon variously changing the combination of a contrast medium concentration, an injection rate, a blood vessel diameter, and X-ray conditions and calculating a blood vessel contrast for each combination of a contrast medium concentration, an injection rate, a blood vessel diameter, and X-ray conditions.

An example of a method of inputting planned values of contrast medium concentration, injection rate, and blood vessel diameter will be described next.

Figure 4:
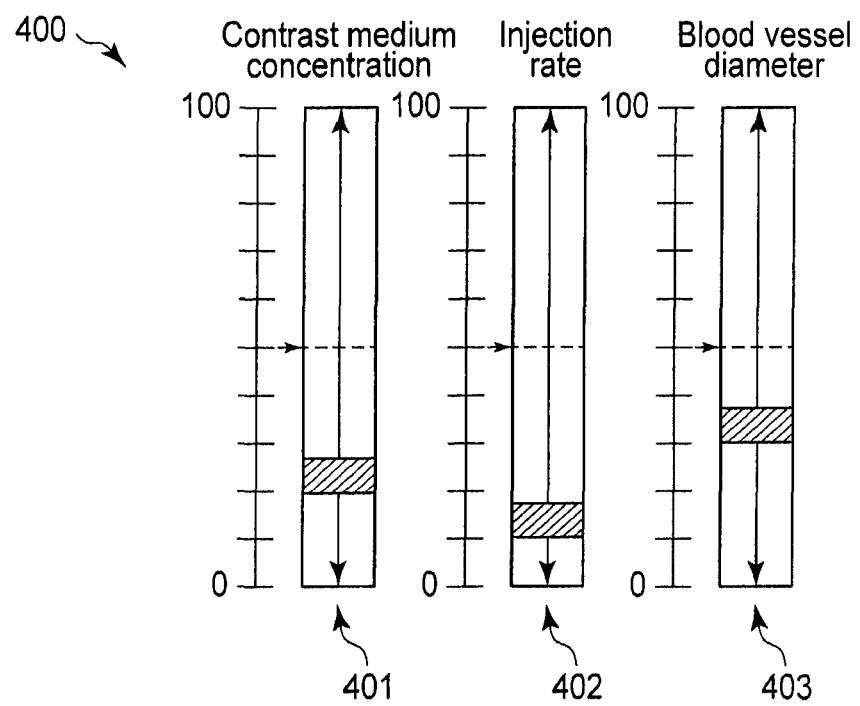
FIG. 4 is a view showing an example of the input window displayed on the monitor device shown in FIG. 1.

In one example, the user inputs planned values of contrast medium concentration, injection rate, and blood vessel diameter with an input window 400 displayed on the monitor devices 153, which is shown in FIG. 4. The input window 400 displays a slider 401 for designating a planned value of contrast medium concentration, a slider 402 for designating a planned value of injection rate, and a slider 403 for designating a planned value of blood vessel diameter. The user can continuously change planned values of contrast medium concentration, injection rate, and blood vessel diameter by moving the sliders 401, 402, and 403 with the mouse or the like of the operation unit 170.

For the sake of simplicity, FIG. 4 shows an example of designating values in the range from 0 to 100 by moving each of the sliders 401, 402, and 403. In this case, the larger the value of each slider, the larger the planned value to be input. In general, as the concentration of contrast medium injected increases, the blood vessel contrast on an angiographic image increases. Likewise, as the injection rate of a contrast medium increases, and the diameter of a blood vessel through which the contrast medium flows increases, the blood vessel contrast on an angiographic image increases. The arrows and broken lines shown in FIG. 4 indicate the initial positions of the sliders. Referring to FIG. 4, each initial position is set at a position indicating the median value of a corresponding set range. Displaying each slider at the initial position in this manner allows the operator to visually recognize how much he/she has moved the slider. Note that each initial position may be set at a position indicating an arbitrary value, and the respective initial positions may be set at different positions in the contrast medium concentration, injection rate, and blood vessel diameter ranges.

Figure 5:
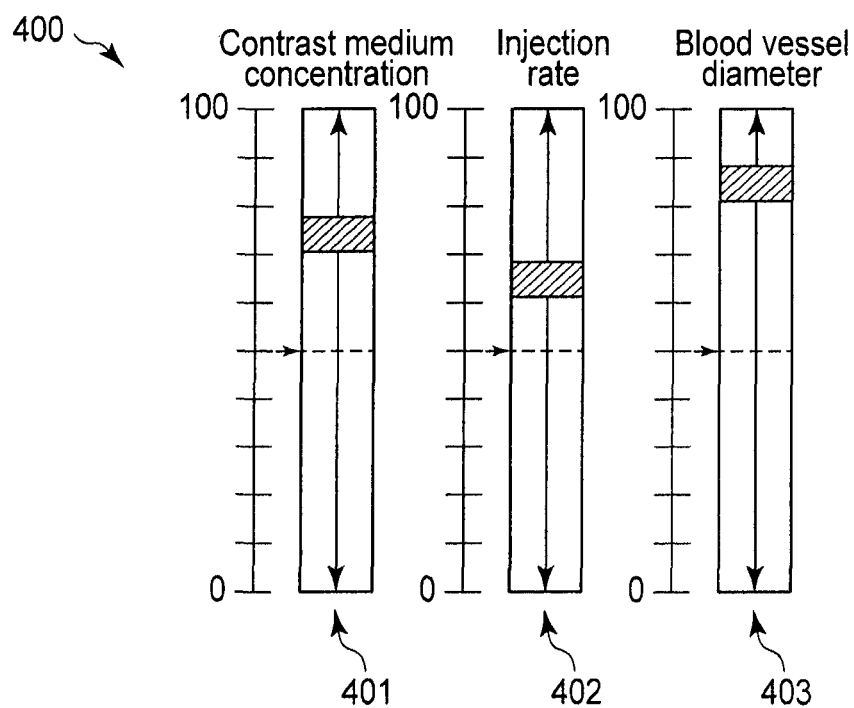
FIG. 5 is a view showing an input window after the sliders shown in FIG. 4 are operated.
Figure 6:
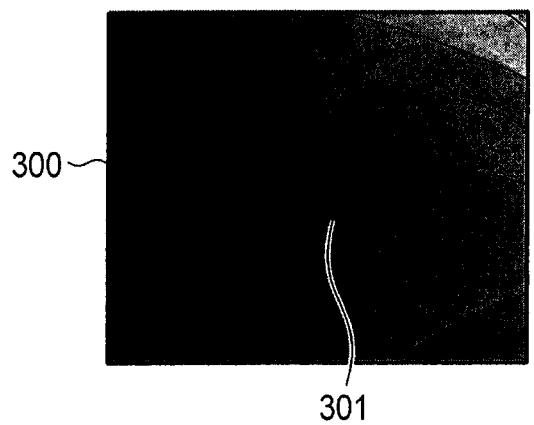
FIG. 6 is a view for explaining how the density of an ROI changes accompanying the operation of the sliders shown in FIG. 4.

In the embodiment, when the operator changes the planned values of contrast medium concentration, injection rate, and blood vessel diameter to be input, the apparatus acquires a blood vessel contrast by referring to the clinic database 181 based on the planned values of contrast medium concentration, injection rate, and blood vessel diameter after the change. The density of the ROI on the X-ray image 300 before injection of the contrast medium changes in accordance with this blood vessel contrast. For example, when the operator changes the values of the sliders 401, 402, and 403 to larger values as shown in FIG. 5, the blood vessel contrast acquired by the blood vessel contrast acquisition unit 180 increases. As a consequence, as shown in FIG. 6, the displayed ROI 301 on the X-ray image 300 becomes darker (blacker).

FIGS. 4 and 5 show values from 0 to 100 at scale marks of the respective planned values for convenience sake. In practice, however, values associated with contrast medium concentrations, injection rates, and blood vessel diameters are displayed at the respective scale marks. For example, values in the range from 1 ml/sec to 5 ml/sec are displayed at the respective scale marks associated with injection rates. The values displayed at the scale marks of the respective planned values may be fixed or may be changed occasionally in reflection with information from the injector 190.

It is possible to supply the planned values of contrast medium concentration and injection rate, input by the user and stored in the condition storage unit 182, to the injector 190 via the system control unit 101. In this case, the injector 190 sets contrast medium conditions in accordance with the planned values of contrast medium concentration and injection rate received from the condition storage unit 182. The injector 190 adjusts the contrast medium to a concentration corresponding to the contrast medium conditions, and injects the contrast medium into the object 132 at an injection rate corresponding to the contrast medium conditions.

A series of operations of predicting and displaying a blood vessel contrast on an angiographic image before capturing of the angiographic image will be described next with reference to FIGS. 1 and 7.

In step S701 in FIG. 7, the image data generation unit 140 generates image data of the object 132.

More specifically, first of all, the object 132 is placed on the top 131 of the bed 202. When the system control unit 101 gives a movement control instruction to the C-arm/top mechanism control unit 161, the C-arm/top mechanism control unit 161 sends driving signals to the top moving mechanism 162 and the C-arm pivoting/moving mechanism 163. The top moving mechanism 162 is operated by the driving signal to adjust the top 131 to a desired position. In addition, the C-arm pivoting/moving mechanism 163 is operated by the driving signal to adjust the C-arm 130 to a desired position and angle.

The system control unit 101 sends X-ray irradiation commands to the X-ray control unit 116 and the X-ray generation unit 110. With this operation, the X-ray control unit 116 generates a voltage application control signal for the generation of a voltage designated by preset X-ray conditions and sends the signal to the high-voltage generator 117. The high-voltage generator 117 generates a high voltage corresponding to the voltage application control signal from the X-ray control unit 116, and applies the voltage to the X-ray generation unit 110. The X-ray generation unit 110 generates X-rays upon receiving the high voltage applied from the high-voltage generator 117. The X-rays from the X-ray generation unit 110 are directed to the object 132.

The X-rays emitted from the X-ray tube 111 pass through the X-ray stop unit 112, are transmitted through the object 132, and are incident on the planar detector 121. The X-rays incident on the planar detector 121 are converted into charges and stored by the semiconductor detection elements. The stored charges are read by driving pulses from the gate driver 122. The charge/voltage converter 123 converts the read charges into a voltage signal. The analog-to-digital converter 124 converts the voltage signal from the charge/voltage converter 123 into a digital signal, and outputs it as projection data. The image data generation unit 140 generates image data of the object 132 based on the projection data acquired in this manner.

The apparatus performs X-ray imaging in step S701 without injecting any contrast medium into the object 132 to perform, for example, positioning. The image data generated in step S701 is image data before injection of the contrast medium (that is, non-enhanced image data) associated with the object 132. The embodiment exemplifies a case in which image data before injection of a contrast medium which is used for the prediction of a blood vessel contrast is a fluoroscopic image (still image). However, the image data to be used is not limited to this, and it is possible to use moving image data obtained by continuously capturing fluoroscopic images.

In step S702, the system control unit 101 displays the image data of the object 132, generated by the image data generation unit 140, as an X-ray image on the monitor device 153 of the display unit 150. In step S703, the user operates the operation unit 170 to set an ROI on an X-ray image. The user sets an ROI on the X-ray image so as to include, for example, a blood vessel as an examination or treatment target. In step S704, the calculation unit 143 calculates the average pixel value of the ROI on the X-ray image.

In step S705, the system control unit 101 acquires X-ray conditions applied to the next X-ray imaging operation using a contrast medium, and acquires the initial values of the planned values of contrast medium concentration, injection rate, and blood vessel diameter. For example, the X-ray conditions acquired in step S705 are the same as those applied to the X-ray imaging operation before injection of the contrast medium in step S701. Assume that the initial values of the planned values of contrast medium concentration and injection rate are the values of contrast medium concentration and injection rate set in the injector 190. Assume that in the embodiment, the initial value of the planned value of blood vessel diameter is the value preset in the system control unit 101.

In step S706, the condition storage unit 182 stores the acquired X-ray conditions and the planned values of contrast medium concentration, injection rate, and blood vessel diameter. In step S707, the blood vessel contrast acquisition unit 180 refers to the clinic database 181 based on the X-ray conditions and the planned values of contrast medium concentration, injection rate, and blood vessel diameter stored in the condition storage unit 182 to acquire a blood vessel contrast specified by the X-ray conditions and the planned values of contrast medium concentration, injection rate, and blood vessel diameter.

In step S708, the calculation unit 143 calculates the predictive average pixel value of the ROI based on the average pixel value of the ROI calculated in step S704 and the blood vessel contrast acquired in step S707. The calculation unit 143 calculates a predictive average pixel value P1 of the ROI from a blood vessel contrast C acquired in step S707 and an average pixel value P0 of the ROI calculated in step S704, according to, for example, equation (1).

In step S709, the system control unit 101 controls the monitor device 153 to superimpose and display a partial image having the calculated predictive average pixel value on the ROI on the X-ray image. For example, the image data generation unit 140 generates image data by replacing the pixel value of each pixel in the ROI on the X-ray image with the predictive average pixel value calculated in step S708 in accordance with an instruction from the system control unit 101, and sends the image data to the display unit 150.

In step S710, the apparatus determines whether the user has operated the operation unit 170 to change at least one of the planned values of contrast medium concentration, injection rate, and blood vessel diameter. For example, immediately after the initial values of the planned values of contrast medium concentration, injection rate, and blood vessel diameter are acquired in step S705, the sliders 401, 402, and 403 shown in FIG. 4 are set to values corresponding to the initial values. The user moves the sliders 401, 402, and 403 to input or change the planned values of contrast medium concentration, injection rate, and blood vessel diameter. When the user has changed at least one of the planned values of contrast medium concentration, injection rate, and blood vessel diameter, the process returns to step S706 to store the planned values of contrast medium concentration, injection rate, and blood vessel diameter in the condition storage unit 182.

When the condition storage unit 182 stores the planned values of contrast medium concentration, injection rate, and blood vessel diameter after the change, the apparatus performs the processing in step S707 and the subsequent steps described above again. That is, the blood vessel contrast acquisition unit 180 newly acquires a blood vessel contrast by referring to the clinic database 181 based on the X-ray conditions and the planned values of contrast medium concentration, injection rate, and blood vessel diameter stored in the condition storage unit 182 (step S707). The calculation unit 143 recalculates the predictive average pixel value of the ROI based on the average pixel value calculated in step S704 and the blood vessel contrast newly acquired in step S707 (step S708). The display unit 150 then displays a partial image having the recalculated predictive average pixel value on the ROI on the X-ray image (step S709).

The user adjusts the planned values of contrast medium concentration, injection rate, and blood vessel diameter so as to obtain a desired blood vessel contrast while checking the density of the displayed ROI. That is, the processing from step S706 to Step S710 is repeated until a desired blood vessel contrast is obtained.

If the apparatus determined in step S710 that none of the planned values of contrast medium concentration, injection rate, and blood vessel diameter has been changed, the process advances to step S711. In step S711, the system control unit 101 sets the planned values of contrast medium concentration and injection rate stored in the condition storage unit 182 as contrast medium conditions in the injector 190. The injector 190 generates a contrast medium with a concentration corresponding to the contrast medium conditions. With the above operation, the series of operations shown in FIG. 7 is terminated.

In this manner, the X-ray diagnostic apparatus 100 can predict a blood vessel contrast on the angiographic image generated by X-ray imaging using the contrast medium under the conditions designated by the user, and display the prediction result as an ROI density on an X-ray image before injection of the contrast medium. The user checks the density of the displayed ROI, and determines the planned values of contrast medium concentration and injection rate which allow to obtain a desired blood vessel contrast as a contrast medium concentration and injection rate for the execution of angiography.

As described above, the X-ray diagnostic apparatus 100 according to the embodiment includes the clinic database 181 which holds a correspondence table describing the relationship between blood vessel contrasts and X-ray conditions, contrast medium concentrations, injection rates, and blood vessel diameters. This makes it possible to predict the blood vessel contrast which is obtained when capturing an angiographic image under the conditions designated by the user and display the prediction result as the density of the ROI set on the X-ray image before injection of the contrast medium. By checking the density of the displayed ROI, the user can determine a proper contrast medium concentration and injection rate before capturing of an angiographic image. This makes it possible to prevent unnecessary injection of a contrast medium into the object.

Second Embodiment

In the first embodiment, the initial value of blood vessel diameter is set in advance. In contrast to this, a second embodiment is configured to detect a blood vessel included in the ROI set on an X-ray image and use the diameter of the detected blood vessel as the initial value of blood vessel diameter.

Figure 8:
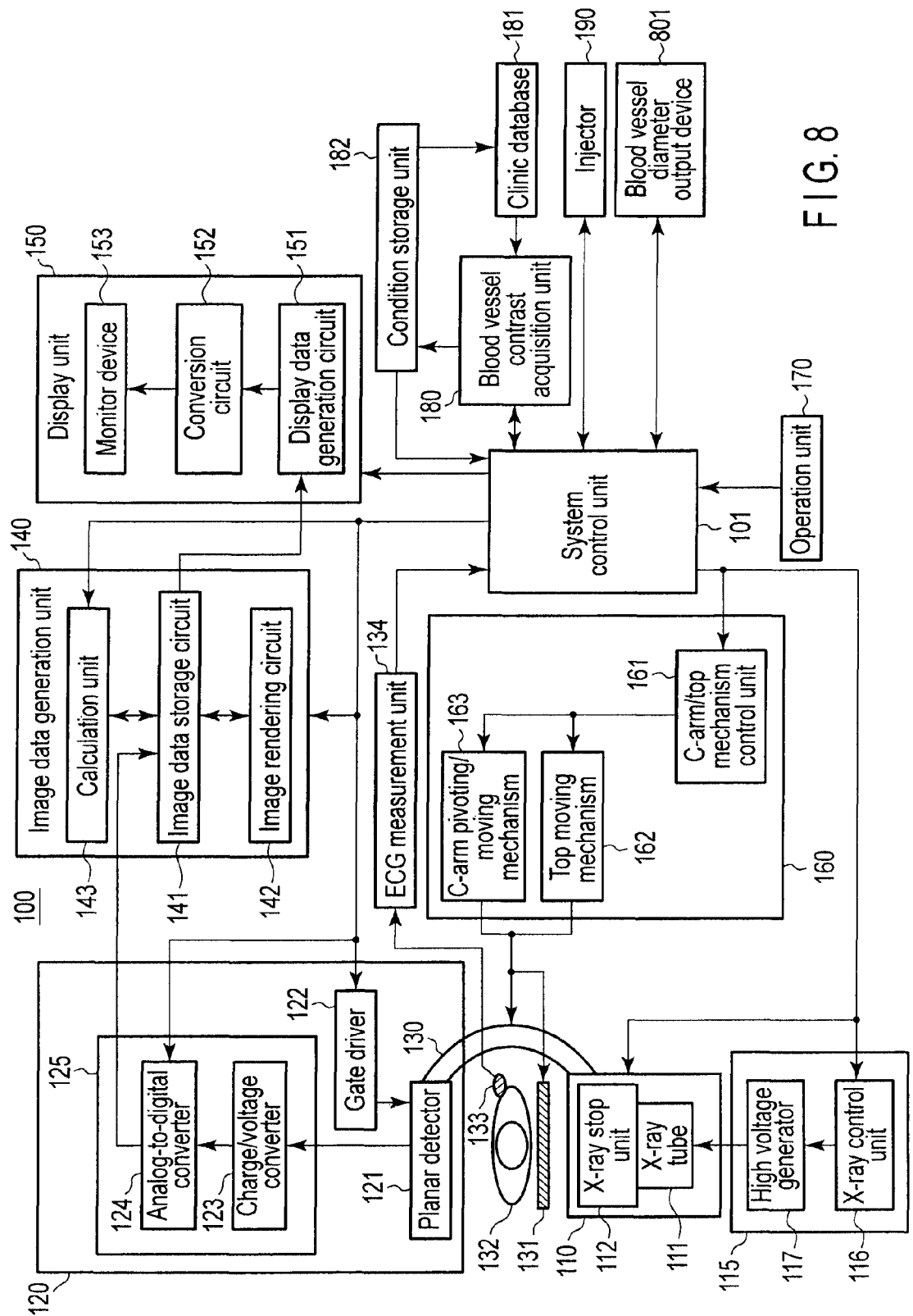
FIG. 8 is a block diagram schematically showing an X-ray diagnostic apparatus according to the second embodiment.

FIG. 8 schematically shows an X-ray diagnostic apparatus 800 according to the second embodiment. In addition to the arrangement of the X-ray diagnostic apparatus 100 shown in FIG. 1, the X-ray diagnostic apparatus 800 shown in FIG. 8 includes a blood vessel diameter output device 801 which detects a blood vessel included in an ROI and outputs the diameter of the blood vessel. In the embodiment, upon detecting a plurality of blood vessels in an ROI, the blood vessel diameter output device 801 outputs the diameter of the thickest blood vessel among the detected blood vessels.

FIG. 9 shows the blood vessel diameter output device 801 in more detail. As shown in FIG. 9, the blood vessel diameter output device 801 includes an X-ray image input unit 901, a CT (Computed Tomography) image input unit 902, an image positioning unit 903, and a blood vessel diameter determination unit 904. The X-ray image input unit 901 receives the X-ray image data generated by an image data generation unit 140. The CT image input unit 902 receives the three-dimensional CT image data captured by an X-ray CT apparatus (not shown). The CT image input unit 902 supplies the three-dimensional CT image data to the blood vessel diameter determination unit 904. In addition, the CT image input unit 902 projects the three-dimensional CT image data on two-dimensional CT image data and supplies the resultant data to the image positioning unit 903. The image positioning unit 903 performs positioning by using X-ray image data and two-dimensional CT image data. The image positioning unit 903 performs positioning by aligning the bone and organ of the X-ray image data with the bone and organ of the CT image.

The blood vessel diameter determination unit 904 receives the positioning result and two-dimensional image data from the image positioning unit 903, receives the three-dimensional CT imaged data from the CT image input unit 902, and receives ROI position information indicating the position of the ROI from a system control unit 101. The blood vessel diameter determination unit 904 determines the position of the ROI on the two-dimensional CT image based on the OI position information, and determines the position of the ROI on the three-dimensional CT image from the position of the ROI on the two-dimensional CT image. The blood vessel diameter determination unit 904 detects a blood vessel included in the three-dimensional CT image and outputs the detected blood vessel diameter.

An example of a blood vessel detection method executed by the blood vessel diameter determination unit 904 will be briefly described. First of all, the blood vessel diameter determination unit 904 extracts a blood vessel region from three-dimensional CT image data, and generates three-dimensional CT image data by erasing information other than the extracted blood vessel region. That is, the blood vessel diameter determination unit 904 generates three-dimensional CT image data in which the pixel values in a region other than a blood vessel region are set to 0. The blood vessel diameter determination unit 904 searches this three-dimensional CT image for pixels having pixel values other than 0. Upon finding a region of pixels having pixel values other than 0 in the ROI, the blood vessel diameter determination unit 904 determines the region as a blood vessel. If there is no pixel having a pixel value other than 0 in the ROI, the blood vessel diameter determination unit 904 increases the size of the ROI until it includes a region of pixels having pixel value other than 0. The system control unit 101 sends information indicating a change in the size of the ROI to a monitor device 153. This information is then reflected in the X-ray image displayed on the monitor device 153.

Note that the blood vessel diameter output device 801 is not limited to an example of using X-ray CT image data, and it is possible to use MR (Magnetic Resonance) images acquired in advance, three-dimensional blood angiographic pictures acquired in advance, or the like. The blood vessel diameter output device 801 is not limited to the example shown in FIG. 9, and may take any form as long as it can detect a blood vessel included in an ROI and output its diameter.

FIG. 10 shows an example of image processing performed by the X-ray diagnostic apparatus 800. The image processing sequence shown in FIG. 10 is equivalent to the procedure in FIG. 7 with step S1001 being added between steps S703 and S704. In this case, a description of the same portions as in FIG. 7 will be omitted as needed, and portions of the procedure different from those in FIG. 7 will be described.

Referring to FIG. 10, in step S701, the image data generation unit 140 generates image data of an object 132 captured before injection of a contrast medium. In step S702, the monitor device 153 of a display unit 150 displays an X-ray image based on the X-ray image data. In step S703, an ROI is set on the X-ray image by the user. When an ROI is set on the X-ray image in step S703 in FIG. 10, the process advances to step S1001.

In step S1001, the blood vessel diameter output device 801 detects a blood vessel included in the set ROI and acquires the diameter of the blood vessel (blood vessel diameter). In step S704, the average pixel value of the ROI is calculated. In step S705, the system control unit 101 acquires X-ray conditions and the initial values of the planned values of contrast medium concentration, injection rate, and blood vessel diameter. In the present embodiment, the initial value of the planned value of blood vessel diameter acquired in step S705 is the blood vessel diameter acquired in step S1001.

The processing in step S706 and the subsequent steps in FIG. 10 is the same as that described with reference to FIG. 7, and a description thereof will not be repeated. Note that since the blood vessel diameter output device 801 has accurately acquired the blood vessel diameter in the ROI, since the planned value of blood vessel diameter is fixed to the blood vessel diameter acquired by the blood vessel diameter output device 801, it is possible to make the planned value of blood vessel diameter unchangeable in step S710.

As described above, since the X-ray diagnostic apparatus 800 according to the present embodiment includes the blood vessel diameter output device 801 which acquires the diameter of a blood vessel included in an ROI, it is possible to accurately acquire a blood vessel diameter in the ROI. This makes it possible to more accurately determine an optimal contrast medium concentration and injection rate for the execution angiography.

The first and second embodiments described above have exemplified the case in which the correspondence table held in the clinic database (also referred to as a data storage unit) 181 associates blood vessel contrasts with X-ray conditions, contrast medium concentrations, injection rates, and blood vessel diameters. However, the embodiments are not limited to this. For example, a correspondence table may associate blood vessel contrasts with only contrast medium concentrations and X-ray conditions. In another case, a correspondence table may associate blood vessel contrasts with contrast medium concentrations and other conditions such as the manufactures of contrast media.

In addition, the first and second embodiments have exemplified the case in which one ROI is set on an X-ray image. However, the embodiments are not limited to this, and it may be set a plurality of ROIs on an X-ray image. Furthermore, the user may manually change a set ROI to an arbitrary position on an X-ray image, as needed. When, for example, the position of an ROI is changed in the second embodiment, the apparatus detects the diameter of the thickest blood vessel among the blood vessels included in the ROI after the change, and automatically change the slider 403, which inputs a blood vessel diameter, to a value corresponding to the detected blood vessel diameter.

The above embodiments have exemplified the arrangement in which the X-ray diagnostic apparatus includes the image processing apparatus which executes the above image processing. However, each embodiment can include an image processing apparatus as an independent apparatus. An image processing apparatus according to an embodiment includes an image data generation unit 140, a display unit 150, an operation unit 170, a blood vessel contrast acquisition unit 180, a clinic database 181, a condition storage unit 182, and a control unit (corresponding to the system control unit 101) which controls the respective units. This image processing apparatus externally receives the data of an X-ray image of an object before injection of a contrast medium, and executes image processing described above based on the received X-ray image data.

Each function of the image processing apparatus according to the embodiment may also be implemented by installing control programs including instructions for the execution of the above image processing in a computer such as a workstation and expanding the control program in a memory. This control program is recorded on a recording medium such as magnetic disks (e.g., a hard disk), optical disks (CD-ROMs, DVDs, and the like), and semiconductor memories. The recording medium to be used is not limited to the above examples, and it is possible to use recording media in any forms as long as they are computer-readable recording media. In addition, the control program need not always be recorded on a recording medium in advance and may be provided by being downloaded via a communication network such as the Internet.

While certain embodiments have been described, these embodiments have been presented by way for example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:
1. An image processing apparatus comprising:
a display unit configured to display an X-ray image;
a data storage unit configured to store a correspondence table describing a relationship between blood vessel contrasts and reference contrast medium concentrations, reference injection rates, reference blood vessel diameters, and reference X-ray conditions;

an input unit configured to receive input information including a planned value of a concentration of a contrast medium planned to be injected, a planned value of injection rate, a planned value of a blood vessel diameter, and an X-ray condition planned to be applied when an angiographic image is captured;

an acquisition unit configured to acquire a blood vessel contrast by referring to the correspondence table based on the planned value of the concentration of the contrast medium planned to be injected, the planned value of injection rate, the planned value of blood vessel diameter, and the X-ray condition;

a calculation unit configured to calculate a predictive pixel value of a region of interest set on the X-ray image based on the acquired blood vessel contrast and a pixel value of the region of interest; and a control unit configured to control the display unit to display the X-ray image while superimposing a partial image having the calculated predictive pixel value on the region of interest.

2. The apparatus according to claim 1, further comprising a blood vessel diameter output device configured to detect a blood vessel included in the region of interest and output a diameter of the blood vessel, wherein the diameter of the blood vessel is used as the planned value of blood vessel diameter.

3. The apparatus according to claim 1, wherein a plurality of regions of interest are set on the X-ray image, the plurality of regions of interest including the region of interest.

4. The apparatus according to claim 1, wherein the input unit is configured to change a position of the region of interest on the X-ray image.

5. The apparatus according to claim 1, wherein a plurality of regions of interest are set on the X-ray image, the plurality of regions of interest including the region of interest.

6. The apparatus according to claim 1, wherein the input unit is configured to change a position of the region of interest on the X-ray image.

7. A non-transitory computer readable medium including computer executable instructions, wherein the instructions, when executed by a processor, cause the processor to perform a method comprising:

displaying an X-ray image;

receiving input information including a planned value of a concentration of a contrast medium planned to be injected, a planned value of injection rate, a planned value of a blood vessel diameter, and an X-ray condition planned to be applied when an angiographic image is captured;

acquiring a blood vessel contrast by referring to a correspondence table based on the planned value of the concentration of the contrast medium planned to be injected, the planned value of injection rate, the planned value of blood vessel diameter, and the X-ray condition, the correspondence table describing a relationship between blood vessel contrasts and reference contrast medium concentrations, reference injection rates, reference blood vessel diameters, and reference X-ray conditions;

calculating a predictive pixel value of a region of interest set on the X-ray image based on the acquired blood vessel contrast and a pixel value of the region of interest; and displaying the X-ray image while superimposing a partial image having the calculated predictive pixel value on the region of interest.

8. An X-ray diagnostic apparatus comprising:

an X-ray generation unit configured to generate X-rays;

a detection unit configured to detect X-rays generated from the X-ray generation unit and transmitted through an object;

an image data generation unit configured to generate X-ray image data based on the detected X-rays;

a display unit configured to display the X-ray image data as an X-ray image;

a data storage unit configured to store a correspondence table describing a relationship between blood vessel contrasts and reference contrast medium concentrations, reference injection rates, reference blood vessel diameters, and reference X-ray conditions;

an input unit configured to receive input information including a planned value of a concentration of a contrast medium planned to be injected, a planned value of injection rate, a planned value of a blood vessel diameter, and an X-ray condition planned to be applied when an angiographic image is captured;

an acquisition unit configured to acquire a blood vessel contrast by referring to the correspondence table based on the planned value of the concentration of the contrast medium planned to be injected, the planned value of injection rate, the planned value of blood vessel diameter, and the X-ray condition;

a calculation unit configured to calculate a predictive pixel value of a region of interest set on the X-ray image based on the acquired blood vessel contrast and a pixel value of the region of interest; and a control unit configured to cause the display unit to display the X-ray image while superimposing a partial image having the calculated predictive pixel value on the region of interest.

9. The apparatus according to claim 8, further comprising an injector configured to inject a contrast medium into the object, wherein the control unit sets the planned value of the concentration of the contrast medium planned to be injected in the injector.

* * * * *